United States Patent [19]
Sisler et al.

[11] Patent Number: 5,100,462
[45] Date of Patent: Mar. 31, 1992

[54] METHOD OF COUNTERACTING ETHYLENE RESPONSE BY TREATING PLANTS WITH DIAZOCYCLOPENTADIENE AND DERIVATIVES THEREOF

[75] Inventors: Edward C. Sisler, Raleigh; Sylvia M. Blankenship, Apex, both of N.C.

[73] Assignee: North Carolina State University, Raleigh, N.C.

[21] Appl. No.: 678,466

[22] Filed: Apr. 1, 1991

[51] Int. Cl.$^5$ .................. A01N 33/26; A01N 3/02; C07C 245/12
[52] U.S. Cl. ............................ 71/121; 71/68; 71/79; 71/115; 534/558
[58] Field of Search .................. 71/79, 121, 68; 534/558

[56] References Cited

U.S. PATENT DOCUMENTS 3,879,188  4/1975  Fritz et al. .................. 71/86

OTHER PUBLICATIONS

E. Sisler and C. Wood, "Competition of Unsaturated Compounds with Ethylene for Binding and Action in Plants," *Plant Growth Regulation* 7, 181–191 (1988).
E. Sisler et al., "Competition of Cyclooctenes and Cyclooctadienes for Ethylene Binding and Activity in Plants," *Plant Growth Regulation* 9, 157–164 (1990).

Primary Examiner—Richard L. Raymond
Assistant Examiner—S. Mark Clardy
Attorney, Agent, or Firm—Bell, Seltzer, Park & Gibson

[57] ABSTRACT

A method of inhibiting an ethylene response in a plant is disclosed herein. The method comprises applying to the plant an effective ethylene response-inhibiting amount of diazocyclopentadiene (DACP). Derivatives of DACP given by Formula (I) below may also be employed:

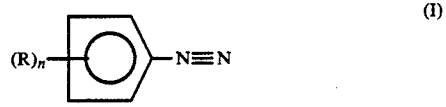

wherein:
  n is from 1 to 4; and
  R is selected from the group consisting of halogen, hydroxy, C1-C4 alkyl, C1-C4 alkoxy, carboxy, and amino. DACP is preferred.

Also disclosed are methods of inhibiting abscission in plants and methods of prolonging the life of cut flowers.

20 Claims, 6 Drawing Sheets

METHOD OF COUNTERACTING ETHYLENE RESPONSE BY TREATING PLANTS WITH DIAZOCYCLOPENTADIENE AND DERIVATIVES THEREOF

FIELD OF THE INVENTION

The present invention generally relates to plant growth regulation, and particularly relates to methods of inhibiting various ethylene responses in plants.

BACKGROUND OF THE INVENTION

Ethylene is known to mediate a variety of growth phenomena in plants. See generally Fritz et al. U.S. Pat. No. 3,879,188. This activity is understood to be achieved through a specific ethylene receptor in plants. Many compounds other than ethylene interact with this receptor: some mimic the action of ethylene; others prevent ethylene from binding and thereby counteract its action.

Many compounds which block the action of ethylene diffuse from the binding site over a period of several hours. See E. Sisler and C. Wood, Plant Growth Reg. 7, 181-191 (1988). These compounds may be used to counteract ethylene action. A problem with such compounds, however, is that exposure must be continuous if the effect is to last for more than a few hours.

Photoaffinity labeling has been used in biological studies to label binding sites in a permanent manner: usually by generating a carbene or nitrene intermediate. Such intermediates are very reactive and react rapidly and indiscriminately with many things. A compound already bound, however, would react mostly to the binding site. In a preliminary study, it was shown that cyclopentadiene was an effective blocking agent for ethylene binding. See E. Sisler et al., Plant Growth Reg. 9, 157-164 (1990). The present invention is based on our continued investigation into compounds capable of photoaffinity labelling the ethylene receptor.

SUMMARY OF THE INVENTION

A method of inhibiting an ethylene response in a plant is disclosed herein. The method comprises applying to the plant an effective ethylene response-inhibiting amount of diazocyclopentadiene.

Another aspect of the present invention is a method of blocking ethylene receptors in plants by applying diazocyclopentadiene to the plants in an effective receptor-blocking amount.

Also disclosed is a method of inhibiting abscission in a plant, comprising applying to the plant an effective abscission-inhibiting amount of diazocyclopentadiene.

Also disclosed is a method of prolonging the life of a cut flower, comprising applying to the cut flower an effective life-prolonging amount of diazocyclopentadiene.

The methods described herein may be carried out in any suitable manner, such as by contacting the plant to diazocyclopentadiene gas, or by spraying the plant with a solution comprised of diazocyclopentadiene. These and other suitable methods of application are discussed in detail below.

Derivatives of diazocyclopentadiene may also be used to carry out the foregoing methods. These derivatives are discussed in detail below.

DETAILED DESCRIPTION OF THE INVENTION

Figure 1:
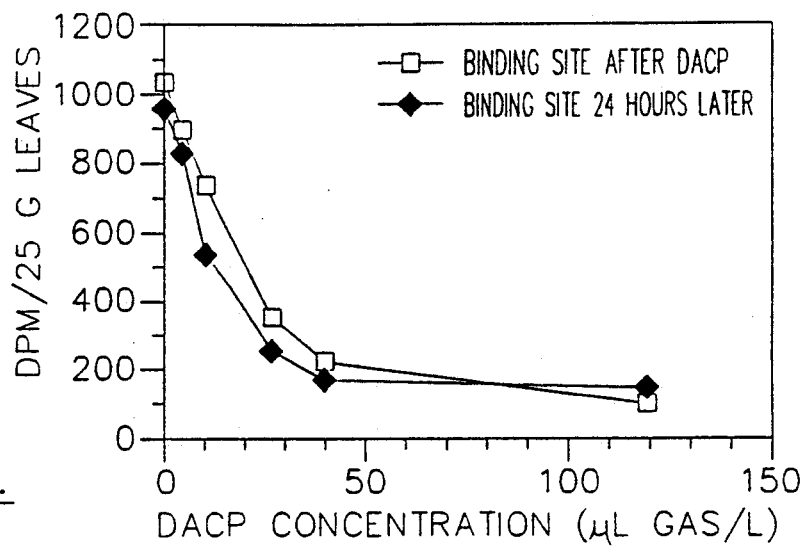
FIG. 1 shows ethylene binding in tobacco leaves after exposure to various concentrations of diazocyclopentadiene (DACP) in the light. Leaves were exposed to DACP for three hours, then assayed for the amount of binding site present with $^{14}$C-ethylene. After 24 hours the leaves were re-assayed for the amount of binding site without retreating with DACP.

In addition to diazocyclopentadiene, various derivatives of diazocyclopentadiene may also be used to carry out the methods set forth herein. These derivatives are defined by Formula (I) below:

(I)

wherein:

n is from 1 to 4; and

R is selected from the group consisting of halogen, hydroxy, C1-C4 alkyl, C1-C4 alkoxy, carboxy, and amino.

In the compounds of Formula (I), n is preferably 1 to 3, more preferably to 2, and most preferably 1. Groups illustrative of halogen include fluoro, bromo, and chloro. Groups illustrative of C1-C4 alkyl include methyl, ethyl, propyl, and butyl, preferably methyl. Groups illustrative of C1-C4 alkoxy include methoxy, ethoxy, propoxy, and butoxy. DACP and the compounds of Formula (I) above are also herein referred to as the "active compound".

The term "plant" is used in a generic sense herein, and encompasses woody-stemmed plants such as trees and shrubs. Plants to be treated by the methods described herein include whole plants and any portions thereof, such as field crops, potted plants, cut flowers (stems with flowers), and harvested fruits and vegetables.

Plants treated by the methods of the present invention are preferably treated with a non-phytotoxic amount of the active compound.

The present invention can be employed to combat numerous different ethylene responses. Ethylene responses include, for example, the ripening abd/or senescence of fruits and vegetables, abscission of foliage, flowers and fruit, the prolongation of the life of ornamentals such as potted plants and cut flowers, in some plants (e.g., pea) the inhibition of growth, and in other plants (e.g., rice) the stimulation of growth.

Vegetables which may be treated by the method of the present invention to inhibit ripening and/or senescence include tomatoes (*Lycopersicon esculentum*), lettuce (e.g., *Lactuea sativa*), soybean (*Glycine max*), green beans (*Phaseolus vulgaris*), lima beans (*Phaseolus limensis*), peas (Lathyrus spp.), and members of the genus Cucumis such as cucumber (*C. sativus*), cantaloupe (*C. cantalupensis*), and musk melon (*C. melo*).

Fruits which may be treated by the method of the present invention to inhibit ripening include apples (*Malus domestica*), bananas (*Musa sapientum*), pears (*Pyrus communis*), papaya (*Carica papaya*), mangoes (*Mangifera indica*), and avocados (*Persea americana*).

Ornamental plants which may be treated by the method of the present invention to prolong flower life and appearance (e.g., delay wilting), include potted ornamentals such as azalea (Rhododendron spp.), hydrangea (*Macrophylla hydrangea*), and hibiscus (*Hibiscus rosasanensis*), and cut flowers such as roses (Rosa spp.), tulips (Tulipa spp.), daffodils (Narcissus spp.), petunias (*Petunia hybrida*), carnation (*Dianthus caryophyllus*), and poinsettia (*Euphorbia pulcherima*).

Plants which may be treated by the method of the present invention to inhibit abscission of foliage, flowers and fruit include cotton (Gossypium spp.), apples, pears, cherries (*Prunus avium*), pecans (*Carva illinoensis*), grapes (*Vitis vinifera*), olives (*Olea europaea*), coffee (*Coffea arabica*) and snapbeans (*Phaseolus vulgaris*).

Additional ethylene responses include those listed in Fritz et al. U.S. Pat. No. 3,879,188 at Column 3 line 62 through Column 6 line 65, the disclosure of which applicants specifically intend to incorporate herein by reference.

After the active compound is applied to the plant, the plant may be exposed to light, whereby the active compound photoaffinity labels the ethylene receptor and the efficacy of the active compound in counteracting ethylene is increased. Any suitable source of light may be employed, including natural light, fluorescent light, and incandescent light.

The active compound of the present invention can be applied to plants by any suitable means. They may be applied alone, or in combination with inert solids such as a dust, or, preferably, suspended in a liquid solution such as an organic solvent or an aqueous solution.

Numerous organic solvents may be used as a carrier for the active compounds of the present invention, e.g., hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, chloroform, trichloroethylene and perchloroethylene, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can be also employed as carriers for the active compound.

The active compounds can be applied as aerosols, e.g., by dispersing them in air by means of a compressed gas such as dichlorodifluoromethane or trichlorofluoromethane and other Freons, for example.

The active compounds of the present invention can also be applied with adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour and lignin.

It may be desirable to incorporate a wetting agent in the compositions of the present invention. Such wetting agents may be employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium salt of the sulfonated monoglyceride of cocoanut fatty acids, sorbitan, sesquioleate, lauryl trimethyl ammonium chloride, octadecyl trimethyl ammonium chloride, polyethylene glycol lauryl ether, polyethylene esters of fatty acids and rosin acids, e.g., Ethofat 7 and 13, sodium N-methyl-N-oleyltaurate, Turkey Red oil, sodium dibutylnaphthalene sulfonate, sodium lignin sulfonate (Marasperse N), polyethylene glycol stearate, sodium dodecylbenzene sulfonate, tertiary dodecyl polyethylene glycol thioether (Nonionic 218), long chain ethylene oxide-propylene oxide condensation products, e.g., Pluronic 61 (molecular weight 1,000), sorbitan sesquioleate, polyethylene glycol ester of tall oil acids, sodium octyl phenoxyethoxyethyl sulfate, polyoxyethylene (20) sorbitan monolaurate ("Tween 20") tris (polyoxyethylene) sorbitan monostearate ("Tween 60"), and sodium dihexyl sulfosuccinate.

The solid and liquid formulations can be prepared by any of the conventional procedures. Thus, the active ingredient, in finely divided form if a solid, may be tumbled together with finely divided solid carrier. Alternatively, the active ingredient in liquid form, including solutions, dispersions, emulsions and suspensions thereof, may be admixed with the solid carrier in finely divided form.

The present invention is explained in greater detail in the following non-limiting Examples. In these examples, μl means microliters; ml means milliliters; l means liters; cm means centimeters; and temperatures are given in degrees Centigrade.

EXAMPLE 1

Preparation of Diazocyclopentadiene (DACP) and Application of DACP Vapor

Diazocyclopentadiene is prepared by the procedure of Doering and DuPuy (W. Doering, C. H. DuPuy, Diazocyclopentadiene, *J. Amer. Chem. Soc.* 75, 5955-5957 (1953) as modified by Weil and Cais (T. Weil, M. Cais, A Simplified Procedure for the Preparation of Diazocyclopentadiene and Some Related Compounds, *J. Org. Chem.* 28, 2472 (1964), or by the procedure of Regitz and Liedhegener (M. Regitz, A. Liedhegener, Reaktionen aktiver methylenerbindungen mit aziden-XV Synthese von diazocyclopentadienem durch diazogruppenubertagung und einige reaktionen, *Tetrahedron* 23, 2701-2708 (1967). The concentration is determined by the use of triphenylphosphine. DACP is kept in a solution of hexane (4-10% DACP). The solution is applied to a paper towel to facilitate evaporation. Values below are given as a gas assuming 282 μl gas/μl (1.059 mg) of liquid.

EXAMPLE 2

Measurement of Ethylene Binding

Plant material was exposed to $^{14}C$-ethylene in the presence or absence of unlabeled ethylene. Usually exposure was for two hours. After this time, material was aired for two minutes and placed in 250 or 500 ml jars containing mercury perchlorate in liquid scintillation vials which also contained fiberglass filter to increase the surface area for 24 hours. The vials were then removed, scintillation fluid added and the samples counted in a liquid scintillation counter. All measurements were corrected for unbound ethylene. When the number of binding sites inactivated by DACP in the light were desired, samples were aired 48 hours before measuring ethylene binding to allow the DACP not undergoing a light reaction to diffuse away.

EXAMPLE 3

Growth and Treatment of Mung Beans

Mung beans (*Vigna radiata* L.) were germinated in the dark for four days. At this point 10-12 sprouts were placed in 3 liter containers, and treated with DACP and ethylene as indicated in the individual Examples below. Ethylene was changed each day and seedlings were retreated with DACP at seven days. The height was measured at ten days. Light was 560 lux throughout the experiment after the four-day germination in the dark.

EXAMPLE 4

Light Treatments

Experiments in the Examples below were carried out under normal laboratory fluorescent lights. The light intensity was 560 lux at the laboratory bench level. Normally treatment was inside 2.5 liter desiccators and the amount of light reaching the plant material was measured to average 448 lux or 80% of the incident light. When more light was needed, desiccators were moved to a position where the intensity was 2700 lux outside the desiccators. The amount of light reaching the plant material was measured to be 2160 lux.

EXAMPLE 5

Effect of Diazocyclopentadiene on Ethylene Binding in Tobacco Leaves

Tobacco leaves (*Nicotiana tabacum* L.) were grown in a greenhouse. Leaves were harvested when approximately 10 cm in length, the midrib removed and allowed to stand overnight for wound ethylene to subside. After incubating tobacco leaves with DACP for three hours under fluorescent lights at 448 lux of fluorescent light, some of the ethylene binding site present, as assayed by $^{14}C$-labeled ethylene disappears. As the concentration of DACP increases, the amount of binding site remaining decreases. The curve (FIG. 1) appears to be biphasic with a decrease of 80% of binding between 0 and 40 μl/l at DACP. Addition of an additional 80 μl/l of DACP reduced binding further 10%. After 24 additional hours, the amount of binding site in the same leaves appears to remain constant. This indicates the binding sites have been permanently inactivated or remain inactive for a very long time. In all previous cases, compounds diffused from the binding site with a half life of three to six hours.

Additional data on the effect of DACP on ethylene binding in mung bean sprouts and tobacco leaves is given in Table 1 below.

TABLE 1
Effect of Diazocyclopentadiene on Ethylene Binding in Mung Bean Sprouts and Tobacco Leaves

| | Binding (% of untreated control) | | | |
| | Mung bean sprouts | | Tobacco leaves | |
| Treatment | Light | Dark | Light | Dark |
|---|---|---|---|---|
| Control | 100 | 100 | 100 | 100 |
| Diazocyclopentadiene | 24 | 100 | 27 | 100 |
| Diazocyclopentadiene + 1000 μl/l Ethylene | — | — | 100 | 100 |
| Diazocyclopentadiene + 4000 μl/l Ethylene | 87 | 97 | 100 | 100 |
| Ethylene | 100 | 100 | 100 | 100 |

Ethylene binding in mung bean sprouts was measured 24 hours after exposure and 48 hours after exposure in tobacco leaves.

EXAMPLE 6

Figure 2A:
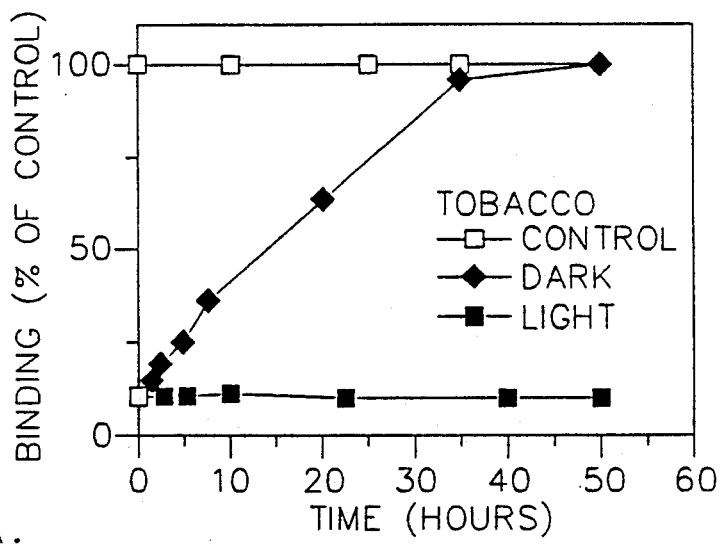
FIG. 2 shows the amount of binding site present in tobacco leaves (FIG. 2A) and mung bean sprouts (FIG. 2B) after treatment of plant material with 245 μl/l (gas) DACP in darkness and subsequently continued in the darkness or exposed to light.

Time Diffusion of Diazocyclopentadiene from Ethylene Binding Site in Tobacco Leaves and Bean Sprouts in Darkness After tobacco leaves are incubated with DACP in darkness, most of the binding site disappears (FIG. 2A). If the DACP is removed, the binding site slowly reappears in the dark with a half life of about 15 hours. If the leaves are preincubated in the light before removing the DACP, the binding site does not reappear or if it does it does so only very slowly over many days. Since tobacco leaves deteriorate after a few days, it was not possible to determine whether the site is regenerated after exposure to light. What is evident is that light causes the binding site to be inactivated for a much longer time in the light than in darkness. It would thus appear that DACP is an effective photoaffinity label.

Figure 2B:
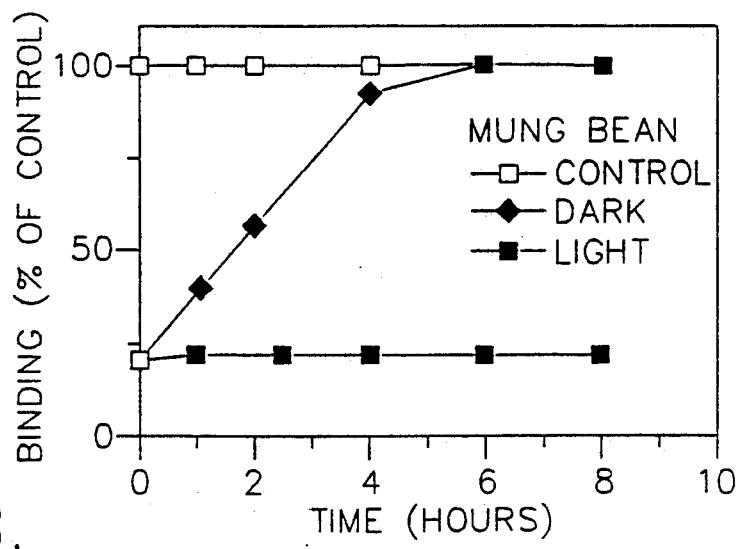

Results with mung bean sprouts (FIG. 2B) are similar to those with tobacco leaves except the time for regeneration of the binding site in darkness is much more rapid. The time for ½ to be regenerated is about two hours.

EXAMPLE 7

Time of Inactivation of Binding Site in Bean Sprouts

Figure 3:
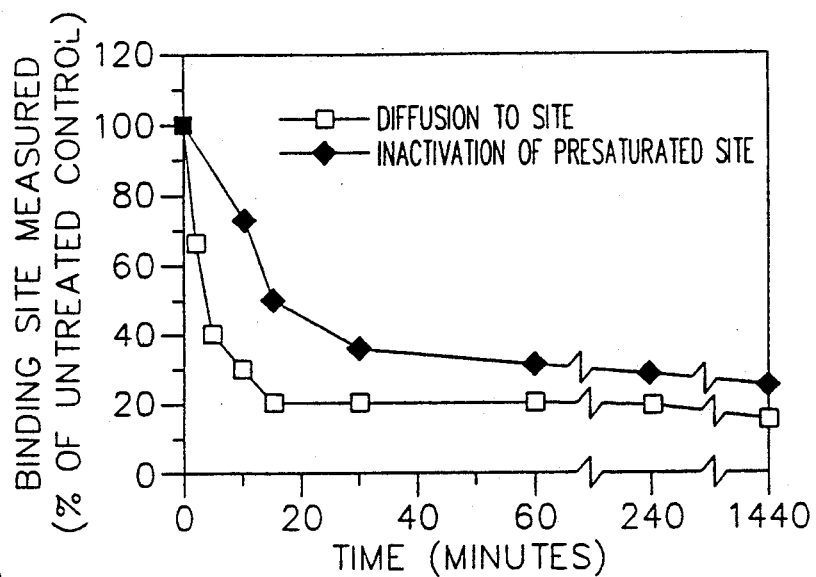
FIG. 3 shows the time of diffusion to the binding site in mung bean sprouts as indicated by the amount of binding site present after exposure to DACP, then to 2160 lux of fluorescent light, and the time of inactivation sites pretreated for two hours with 245 μl/l (gas) DACP and then exposed to 2160 lux of fluorescent light. Sites were assayed 24 hours later using $^{14}$C-ethylene.

After diazocyclopentadiene is released as a liquid it must evaporate and diffuse to the binding site and bind to it. FIG. 3 shows that most of the decrease in binding occurs within 15 minutes in mung bean sprouts. There is a small amount that diffuses to the site and interacts very slowly over a period of many hours.

Once the DACP is bound, the light reaction occurs rapidly (FIG. 3). Most of the reaction has occurred within 30 minutes at 448 lux to a presaturated site. There is a small amount that continues to react with the site slowly. Although no complete study on the effect of light intensity was made, as would be expected, the reaction does occur more rapidly at higher light intensities.

EXAMPLE 8

Figure 4:
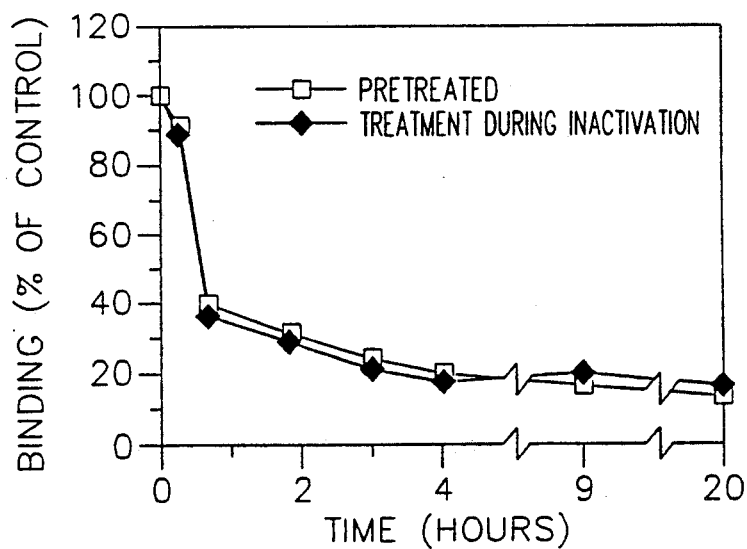
FIG. 4 shows ethylene binding in tobacco leaves treated with DACP. Some leaves were pre-incubated DACP (245 μl/l) in the dark for two hours and then aired for one hour before exposure to 448 lux of fluorescent light. Other leaves were exposed to DACP during the light treatment.

Effect of Pretreatment Versus Diazocyclopentadiene Present During the Light Treatment To determine whether prebound DACP would react as well as DACP present at the time of the reaction, tobacco leaves were allowed to bind DACP for two hours in the dark. After this time the leaves were allowed to air out for one hour in the dark. These were placed in the light at the same time other leaves were treated and placed in the light. No difference in the amount of binding site inactivated was noted. Although this does not prove prebinding is necessary for the reaction to occur, it does show that the background DACP can be removed prior to the light reaction without ill effect, and it may be that only DACP which has previously bound reacts with the binding site or any other component. Similar results were obtained with mung bean sprouts over a number of concentrations (FIG. 4).

EXAMPLE 9

Scatchard Analysis of Ethylene vs. Diazocyclopentadiene Competition

Figure 5:
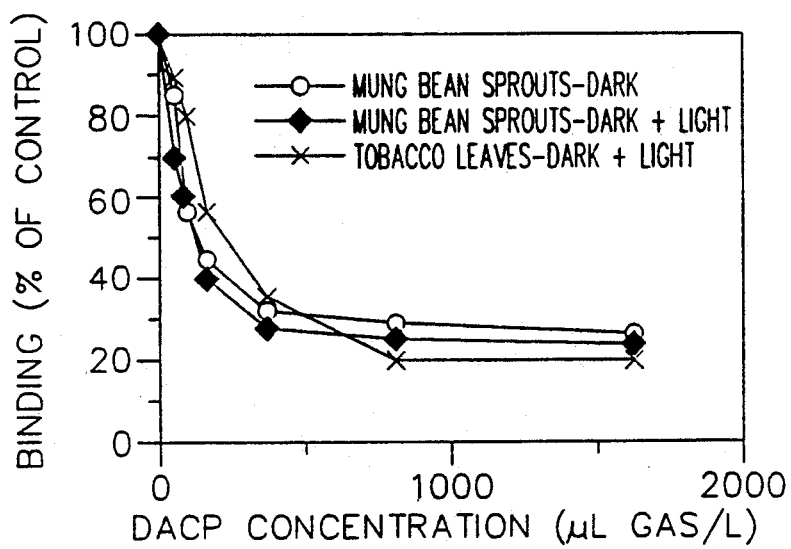
FIG. 5 shows the effect of DACP (245 μl/l gas) on ethylene binding in darkness and light.
Figure 6A:
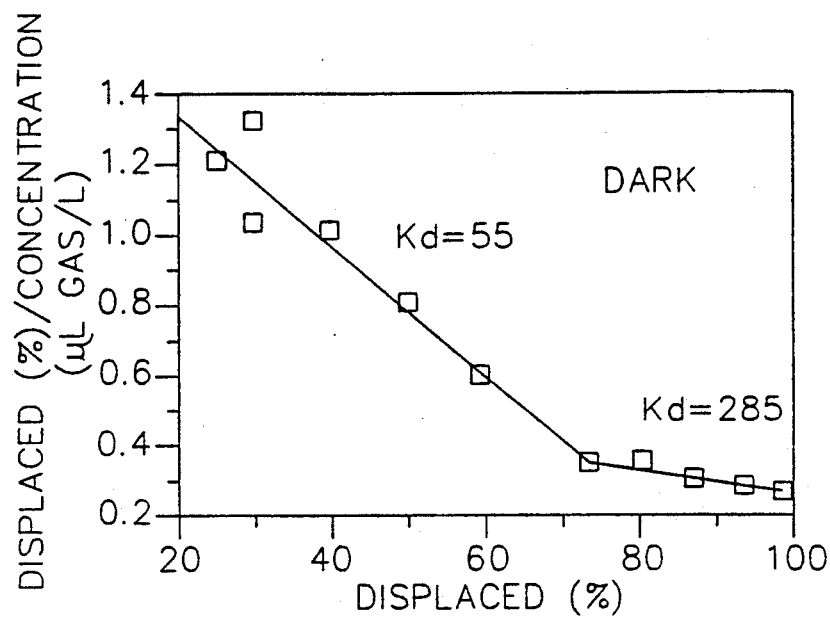
FIG. 6 shows Scatchard plots of DACP-ethylene competition for the ethylene binding sites in tobacco leaves in the dark (FIG. 6A) and in the light (FIG. 6B).
Figure 6B:
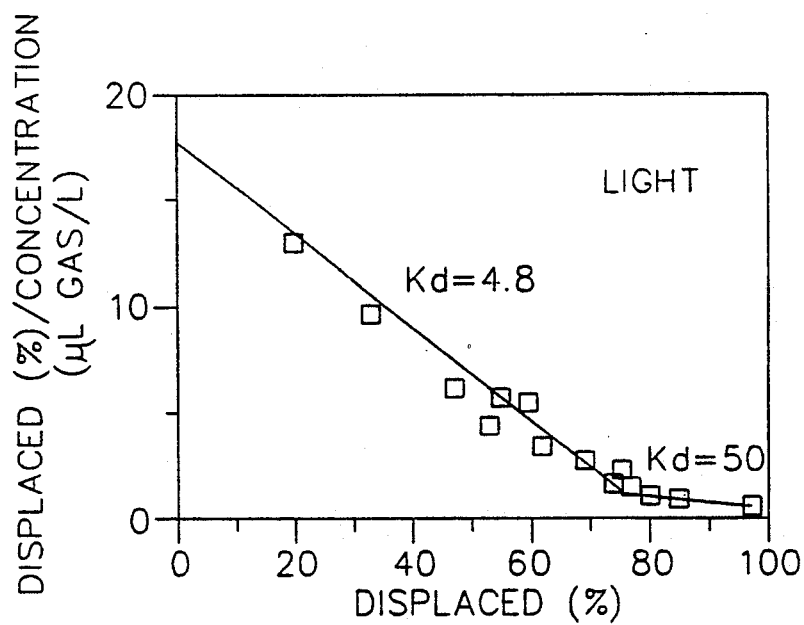
Figure 7A:
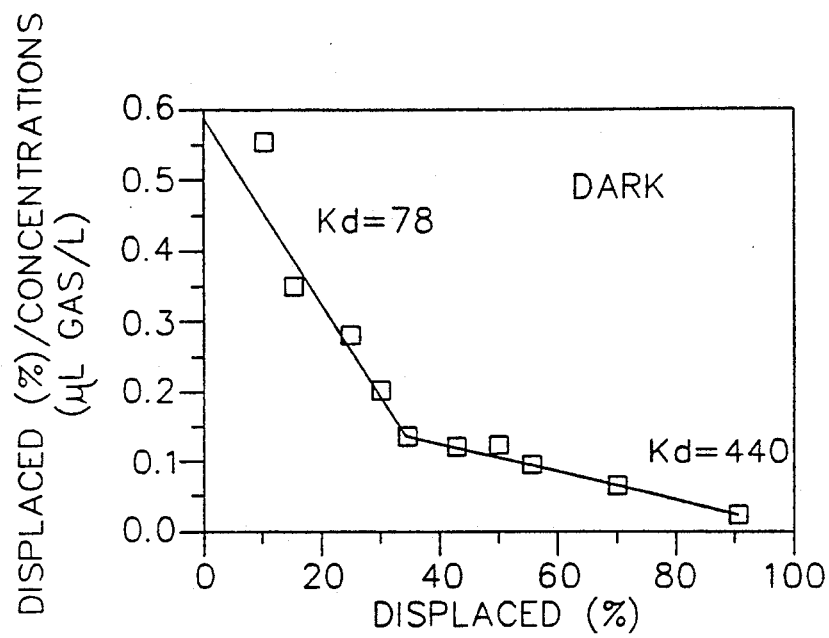
FIG. 7 shows Scatchard plots of DACP-ethylene binding sites in mung bean sprouts in the dark (FIG. 7A) and in the light (FIG. 7B).
Figure 7B:
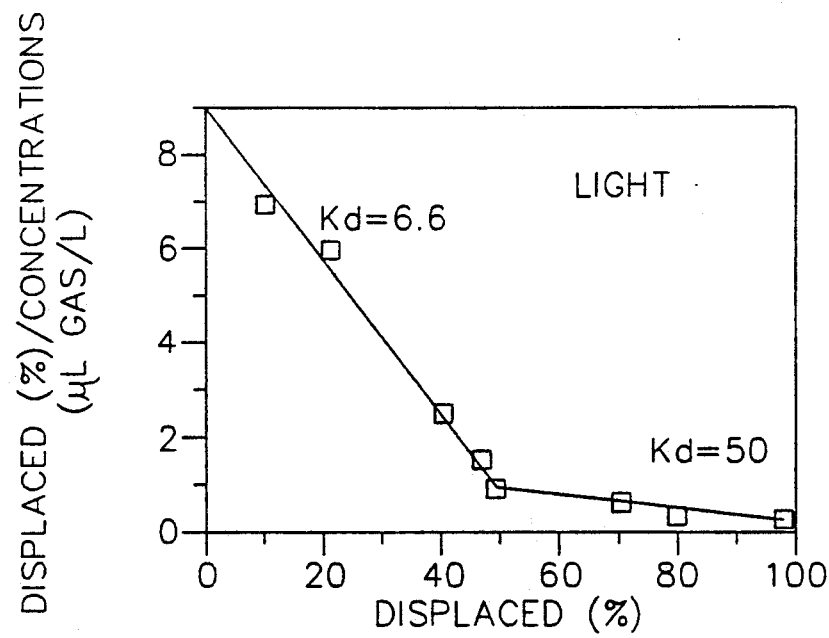

Scatchard plots are used to determine the binding constants of compounds. An underlying assumption using this method is that the reaction is reversible. Using DACP in the light leads to an irreversible complex and the Scatchard plot is not valid. It can be made and compared with the competition in the dark to evaluate the relative effectiveness of the compound in the light versus dark. FIGS. 6 and 7 represent plots for tobacco leaves and mung bean sprouts in the light and in the dark. It can be seen from these two figures that there are apparently two classes of sites present in both tobacco leaves and mung bean sprouts. The values are much lower in the light which would be expected if the site is being permanently removed. A greater portion of the binding sites appears to be occupied in the competition experiments (FIGS. 6, 7) than in experiments in which added ethylene is not present (FIGS. 3, 4, 5). This may be due to the fact that added ethylene occupies a portion of a long-time binding site that does not become apparent in the ethylene binding assay.

To determine the binding constant for physiological activity, bananas were used, and a Lineweaver-Burk plot used to determine $K_1$, the amount of material necessary to double $K_m$. These values are given in Table 2 for application in the light and in darkness.

TABLE 2

Binding Constants for Diazocyclopentadiene and Ethylene

|  |  | LIGHT |  | DARK |  |
|---|---|---|---|---|---|
| Tobacco | $K_d$ (DACP) | 6.6 | 50 | 78 | 440 |
| Mung Bean | $K_d$ (DACP) | 4.8 | 50 | 85 | 285 |
| Banana | $K_i$ (DACP) | 1.2 |  | 40 |  |
| Mung Bean (Untreated) | $K_m$ (Ethylene) | 0.09 |  |  |  |
| Mung Bean (After treatment with DACP) | $K_m$ (Ethylene) | 50 |  |  |  |

EXAMPLE 10

Growth Inhibition of Bean Seedlings

When mung bean seedlings are exposed to ethylene, growth of the seedling is inhibited. A Lineweaver-Burk plot of the growth data gives a ½ maximum of 0.09 of ethylene. After exposure to DACP, growth is inhibited only at much higher concentrations of ethylene (Table 3). A Lineweaver-Burk plot of the data gives a ½ maximum of 50 μl/l of ethylene. This appears to reveal another binding site not previously recognized or either a modification of the previous sight so that it binds at a much higher level. A non-specific effect of the gas is not very likely since much more hexane did not cause inhibition of growth. Since binding data reveal a higher binding site, it is likely that there is a high and a low affinity binding site present that is revealed after the DACP treatment.

TABLE 3

Effect of Diazocyclopentadiene on the Growth of Mung Bean Sprouts

| Treatment | Height (cm) | % of Control |
|---|---|---|
| LIGHT |  |  |
| None | 9.5 | 100 |
| 10 μl/l E | 1.5 | 16 |
| 1000 μl/l E | 1.5 | 16 |
| DACP | 8.9 | 93 |
| DACP + 10 μl/l E | 7.6 | 80 |
| DACP + 100 μl/l E | 5.0 | 53 |
| DACP + 1000 μl/l E | 2.3 | 3.6 |
| DARK |  |  |
| None | 9.5 | 100 |
| 10 μl/l E | 1.5 | 16 |
| DACP | 9.0 | 94 |
| DACP + 10 μl/l E | 1.5 | 16 |

Beans were treated with 120 ul/l as a gas of DACP four days after hydration and retreated after six days. Experiments were conducted under 448 lux of fluorescent light. E means ethylene.

EXAMPLE 11

Effect of Diazocyclopentadiene on Tomato Ripening

Tomato fruit develops a red color as it ripens and the development of this color is dependent on the ethylene induction process. Tomato then is a convenient plant for demonstrating the effectiveness of diazocylopentadiene on ripening.

Plant Material. Tomatoes (*Lycopersicon esculentum*, Mill) were obtained from a wholesale distributor.

Chemicals. DACP was prepared as previously described and kept as a 4-8% solution in hexane. Treatment was in a 3 l container. DACP was pipetted as a hexane solution onto paper towel to facilitate evaporation. After sealing, the containers were kept in darkness or exposed to 448 lux of fluorescent light for 24 hours. After 24 hours, containers were aired out for 24 hours. Those containers kept in darkness were aired in darkness. Subsequently the ethylene treatment was started and all samples were kept in 448 lux of fluorescent light. The gas phase was changed each day.

Ripening. Ripening was measured with an Agtron reflectance spectrophotometer (Magnson Engineers, Inc., Instruments Division, San Jose, Calif.) which measures the ratio of red/green light reflected from the tomato.

Figure 8A:
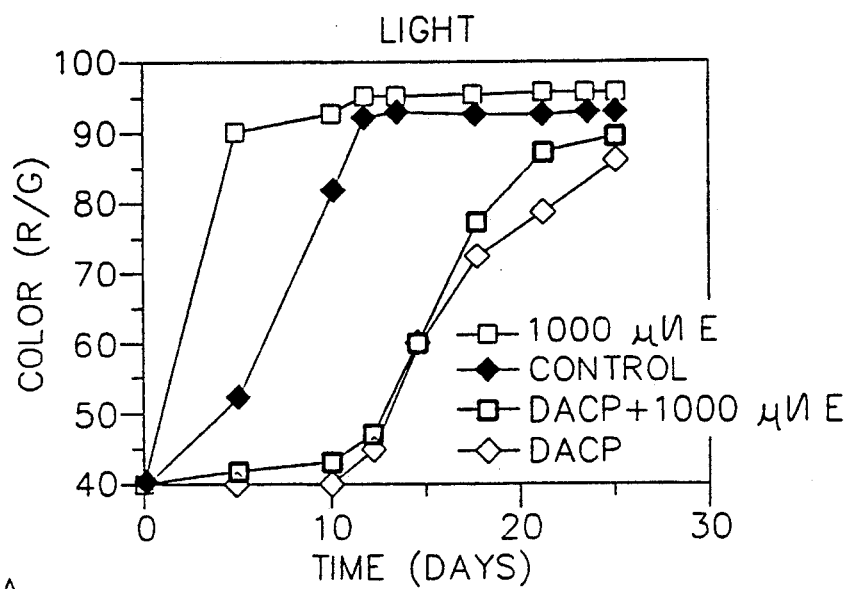
FIG. 8 shows the effect of DACP on ripening of tomato fruit at 25° C. Where indicated, tomatoes were exposed to 185 μl/l (gas) in the light (FIG. 8A) or in the dark (FIG. 8B) with DACP for 24 hours. They were then aired out for 24 hours. After this time ethylene was applied where indicated and all were kept in the light. The tomatoes were aired out each day and the ethylene replaced.
Figure 8B:
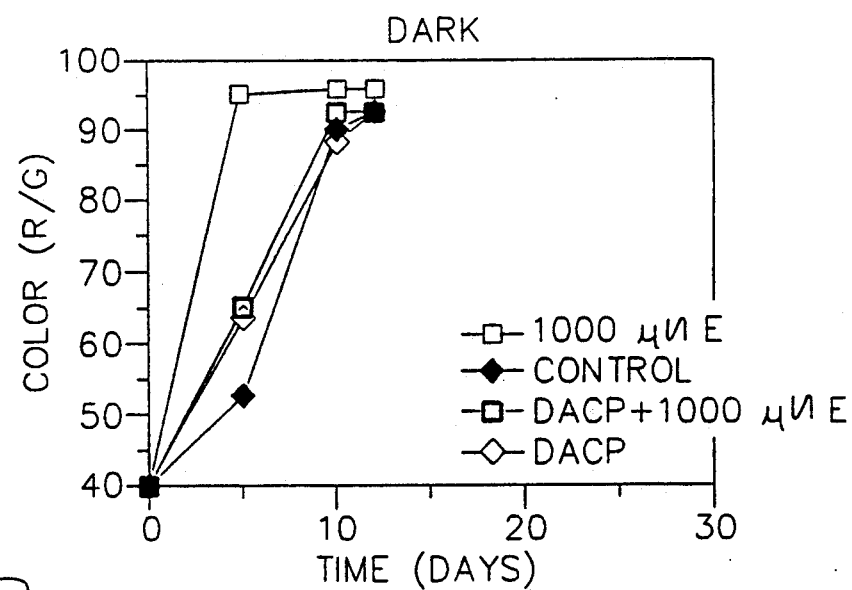
Figure 9:
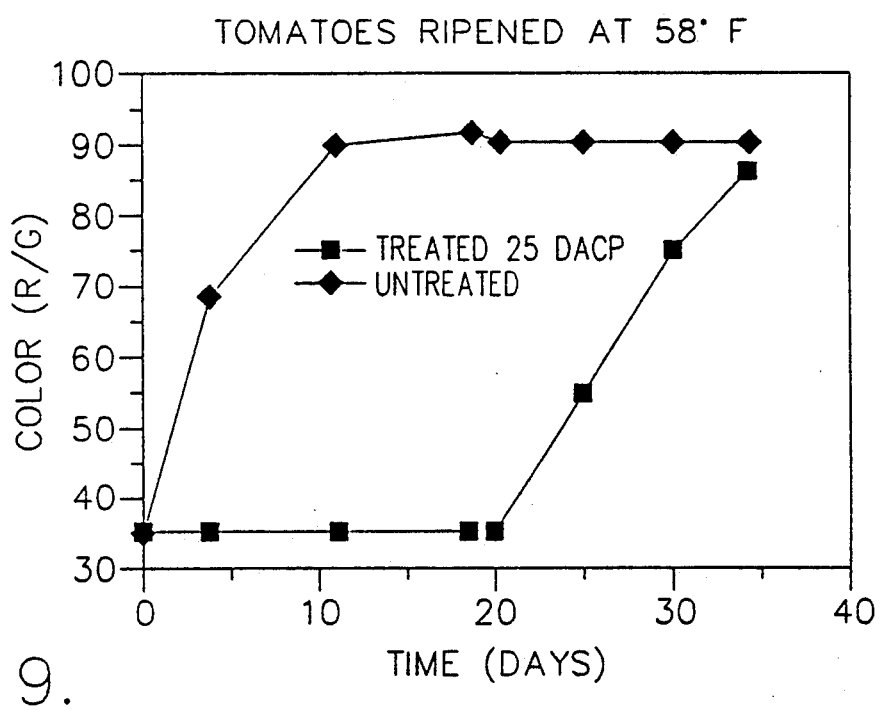
FIG. 9 shows the ripening of tomatoes treated with DACP at 14.5° C.

Effect of DACP on Ripening. FIG. 8 shows the effect of a single exposure of DACP on tomato ripening. At 25° C. the ratio of red to green remained constant for ten days after treatment with DACP whether or not 1000 $\mu l/l$ of ethylene was present. During this time control leaves and ethylene treated leaves ripened. After ten days the treated tomatoes ripened. The ethylene treated tomatoes ripened faster than those without added ethylene and by 25 days all of the tomatoes were nearly ripe. In the dark, DACP had only a small effect and all tomatoes were ripe in ten days as indicated by the red/green ratio. FIG. 9 shows the effect of DACP on tomatoes subsequently kept at 14.5° C.

EXAMPLE 12

Effect of DACP on Cut Flower Longevity

Cut purple petunias (*Petunia hydrida*) are treated with volatile DACP in the same manner as described above. The longevity of the flower is found to increase. Carnation (*Dianthus caryophyllus*) is treated with volatile DACP in like manner, and the longevity of the flower likewise found to increase.

EXAMPLE 13

Effect of DACP on Abscission

Potted poinsettia (*Euphorbia pulcherima*) is treated with volatile DACP in the same manner as described above, and then exposed to ethylene to determine if the DACP would protect the poinsettia from the ethylene. Poinsettia bracts did not abscise in response to our ethylene treatment on any of the plants (including the controls). However, the flowers (cyanthum) died in response to the ethylene in the controls but not on the DACP treated plants. No signs of injury from DACP were seen.

DACP vapor is applied to beans (*Phaseolus vulgaris*) in the same manner as described above and found to prevent ethylene-induced leaf abscission.

The foregoing examples are illustrative of the present invention, and are not to be construed as limiting thereof. The invention is defined by the following claims, with equivalents of the claims to be included therein.

That which is claimed is:

1. A method of inhibiting an ethylene response in a plant, comprising applying to the plant an effective ethylene response-inhibiting amount of a compound of Formula (I) below:

wherein:
n is from 1 to 4; and
R is selected from the group consisting of hydrogen, halogen, hydroxy, C1-C4 alkyl, C1-C4 alkoxy, carboxy, and amino.

2. A method according to claim 1, wherein n is from 1 to 2.

3. A method according to claim 1, wherein said compound is diazocyclopentadiene.

4. A method according to claim 1, wherein said applying step is carried out by contacting said plant to a gas of said compound.

5. A method according to claim 1, wherein said applying step is carried out by spraying said plant with a solution comprising said compound.

6. A method according to claim 1, wherein said ethylene response is fruit ripening.

7. A method according to claim 6, wherein said fruit is selected from the group consisting of apples, bananas, pears, papaya, mangoes, and avocados.

8. A method according to claim 1, wherein said ethylene response is vegetable ripening.

9. A method according to claim 8, wherein said vegetable is selected from the group consisting of melons, tomatoes, lettuce, soybean, grean beans, lima beans, peas, and genus Cucumis.

10. A method of inhibiting abscission in a plant, comprising applying to the plant an effective abscission-inhibiting amount of a compound of Formula (I) below:

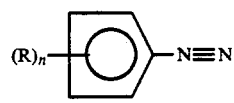

wherein:
n is from 1 to 4; and
R is selected from the group consisting of hydrogen, halogen, hydroxy, C1-C4 alkyl, C1-C4 alkoxy, carboxy, and amino.

11. A method according to claim 10, wherein n is from 1 to 2.

12. A method according to claim 10, wherein said compound is diazocyclopentadiene.

13. A method according to claim 10, wherein said applying step is carried out by contacting said plant to a gas of said compound.

14. A method according to claim 10, wherein said applying step is carried out by spraying said plant with a solution comprising said compound.

15. A method according to claim 10, wherein said plant is selected from the group consisting of cotton, apple, pear, cherry, pecan, grape, olive, coffee, and snapbean.

16. A method of prolonging the life of a cut flower, comprising applying to the cut flower an effective life-prolonging amount of a compound of Formula (I) below:

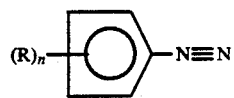

wherein:
n is from 1 to 4; and

R is selected from the group consisting of hydrogen, halogen, hydroxy, C1-C4 alkyl, C1-C4 alkoxy, carboxy, and amino.

17. A method according to claim 16, wherein n is from 1 to 2.

18. A method according to claim 16, wherein said compound is diazocyclopentadiene.

19. A method according to claim 16, wherein said applying step is carried out by contacting said plant to a gas of said compound.

20. A method according to claim 16, wherein said applying step is carried out by spraying said plant with a solution comprising said compound.

* * * * *